United States Patent [19]

Buell

[11] Patent Number: 4,597,760
[45] Date of Patent: Jul. 1, 1986

[54] WASTE-CONTAINMENT GARMENT HAVING DISPOSABLE ELASTICIZED INSERT

[75] Inventor: Kenneth B. Buell, Cincinnati, Ohio

[73] Assignee: The Procter & Gamble Company, Cincinnati, Ohio

[21] Appl. No.: 508,453

[22] Filed: Jun. 27, 1983

[51] Int. Cl.[4] ............................................. A61F 13/16
[52] U.S. Cl. .................................................. 604/397
[58] Field of Search ..................... 604/358, 385, 402

[56] References Cited

U.S. PATENT DOCUMENTS

| | | | |
|---|---|---|---|
| 1,931,357 | 10/1933 | Potwin | 604/399 |
| 2,733,715 | 2/1956 | Folk | 604/398 |
| 3,049,124 | 8/1962 | Thompson | 604/399 |
| 4,211,226 | 7/1980 | Schaar | 604/370 |
| 4,227,531 | 10/1980 | McLeod | 604/396 |
| 4,244,368 | 1/1981 | Caradouna | 604/398 |
| 4,410,327 | 10/1983 | Baggaley | 604/391 |

FOREIGN PATENT DOCUMENTS

| | | | |
|---|---|---|---|
| 558763 | 7/1957 | Belgium | 604/397 |
| 2335165 | 7/1977 | France | 604/391 |

*Primary Examiner*—John D. Yasko
*Attorney, Agent, or Firm*—Thomas J. Slone; Fredrick H. Braun; Richard C. Witte

[57] ABSTRACT

A waste-containment garment comprising a disposable, elasticized waste-containment insert secured inside an over-garment such as a conventional reuseable diaper, or a disposable diaper, or overpants, or the combination of a reuseable diaper covered with overpants. The insert comprises an absorbent core and a liquid impervious backsheet. Preferably, it also includes a liquid pervious, hydrophobic topsheet. The insert has a width less than one-half the midsection girths of intended users and, preferably, the absorbent core has front and back waist portions which have widths of from about fifteen to about thirty-five percent of the midsection girths of intended users or, nominally, about one-quarter of the midsection girth of an average size intended wearer. The insert is so elasticized along its longitudinal side edges that, when properly secured inside a suitable over-garment, and the over-garment is properly applied to a wearer, the elasticized side edges of the insert are sufficiently tensioned to form liquid seals or leg cuffs along upper thigh regions of the wearer: particularly, along the inner spans of the upper thigh regions of the wearer. The insert may include outwardly facing adhesive areas on its corners to enable its securement to inwardly facing surface regions of the over-garment; and the insert may further include captive peelable covers. The insert may, alternatively, be provided with reinforcing grommets on its corners to facilitate fastening it within a snap-fastener equipped overpants or the like; or such grommets may be provided with adhesive coatings and peelable covers to enable the insert to be secured with either its integral adhesive areas or with snap fasteners or the like attached to or integral with overpants.

1 Claim, 21 Drawing Figures

WASTE-CONTAINMENT GARMENT HAVING DISPOSABLE ELASTICIZED INSERT

DESCRIPTION

1. Technical Field

This invention pertains to absorbent pads for external application and supports therefor: for example, disposable diapers but more particularly to a waste-containment garment comprising an elasticized disposable insert in combination with an over-garment such as a reuseable diaper, a disposable diaper, or overpants, and the like. The insert of the present invention may be secured inside such an over-garment with snap-fasteners or the like integrated into the over-garment, or by securement means such as adhesive areas on the insert which are disposed and configured to so secure the insert within a complementary over-garment that the leg cuffs of the insert are sufficiently stretched upon applying the over-garment to a wearer that the leg cuffs of the insert are sealingly engaged with skin areas of the wearer.

2. Background Art

Non-elasticized diaper inserts or liners are shown in a number of U.S. Patents. Representative U.S. patents include U.S. Pat. No. 2,141,105 which issued Dec. 20, 1938, to J. A. Eller et al and shows an absorbent pad secured inside a holder with bands or tapes which may be elastic; U.S. Pat. No. 2,292,030 which issued Aug. 4, 1942 to M. Kraft, U.S. Pat. No. 2,577,398 which issued Dec. 4, 1951 to V. Blake, and U.S. Pat. No. 2,606,558 which issued Aug. 12, 1952 to H. O. Kennette which show liners secured with snap fasteners inside side-closing overpants; U.S. Pat. No. 4,022,210 which issued May 10, 1977 to Jacob A. Glassman and shows a liner secured to a diaper with spots of pressure sensitive adhesive. Additionally, U.S. Pat. No. 2,733,715 which issued Feb. 7, 1956 to Y. L. Folk discloses Composite Training Pants and Diaper having unitized elasticized leg cuffs: leg cuffs wherein the longitudinal side edges of the training pants are joined to the longitudinal side edges of the diaper and jointly elasticized by elastic bands. Also, U.S. Pat. No. 3,860,003 which issued Jan. 14, 1975 to Kenneth Barclay Buell, the inventor of the present invention, discloses an integral disposable diaper having contractable side portions (i.e., elasticized leg cuffs); and U.S. Pat. No. 4,211,226 which issued July 8, 1980 to Charles H. Schaar discloses a disposable diaper with a captive peelable flap covered tape fastener. While these patents disclose liner, diaper and outer-garment configurations and combinations which have solved some of the problems associated with providing waste-containment garments—particularly those comprising liners or inserts—they have not solved the problems to the same extent or degree as enabled by the present invention: i.e., by providing disposable, elasticized waste-containment inserts for use in a variety of over-garments so that the over-garments are protected against soilage by elasticized-leg-cuffs of the inserts. Thus, light capacity inserts embodying the present invention can be used with conventional diapers, disposable diapers, and other suitable over-garments to reduce the frequency of changing the over-garments. That is, for example, the present invention obviates the need to change heavy duty conventional or disposable diapers or the like after light soiling such as by a relatively low volume urine discharge.

DISCLOSURE OF THE INVENTION

In accordance with one aspect of the present invention, a waste-containment garment is provided which comprises an elasticized leg-cuff insert, an over-garment, and means for securing the insert in the over-garment prior to applying the garment to a wearer that, upon applying the garment to a wearer, the leg-cuffs of the insert are sufficiently stretched to sealingly engage them with skin surfaces of the wearer: preferably inwardly facing upper thigh areas of the wearer but which may include outwardly facing upper thigh areas and/or abdominal areas and/or hip areas of the wearer. Preferably, the insert comprises an absorbent core, a liquid impervious backsheet, and elasticized longitudinally extending leg cuffs disposed adjacent longitudinally extending side edges of the core. Such an insert may be rectangular or hourglass shape; may include adhesive means or grommets or a combination thereof disposed on its outwardly facing corners to enable attaching it to an over-garment, or enabling over-garment mounted fasteners to secure the liner within the over-garment. Additionally, such adhesive means may be provided with captive peelable cover means for protecting the adhesive means prior to use, and for obviating severable members which would otherwise present inherent safety problems. Preferably, the over-garment also comprises elasticized leg cuffs so that the garment per se comprises two sets of independently elasticized leg cuffs which are both activated upon applying the garment to a wearer.

BRIEF DESCRIPTION OF THE DRAWINGS

While the specification concludes with claims particularly pointing out and distinctly claiming the subject matter regarded as forming the present invention, it is believed the invention will be better understood from the following descriptions taken in conjunction with the accompanying drawings in which:

FIGS. 10 and 13 are plan views.

DETAILED DESCRIPTION OF THE INVENTION

Figure 1:
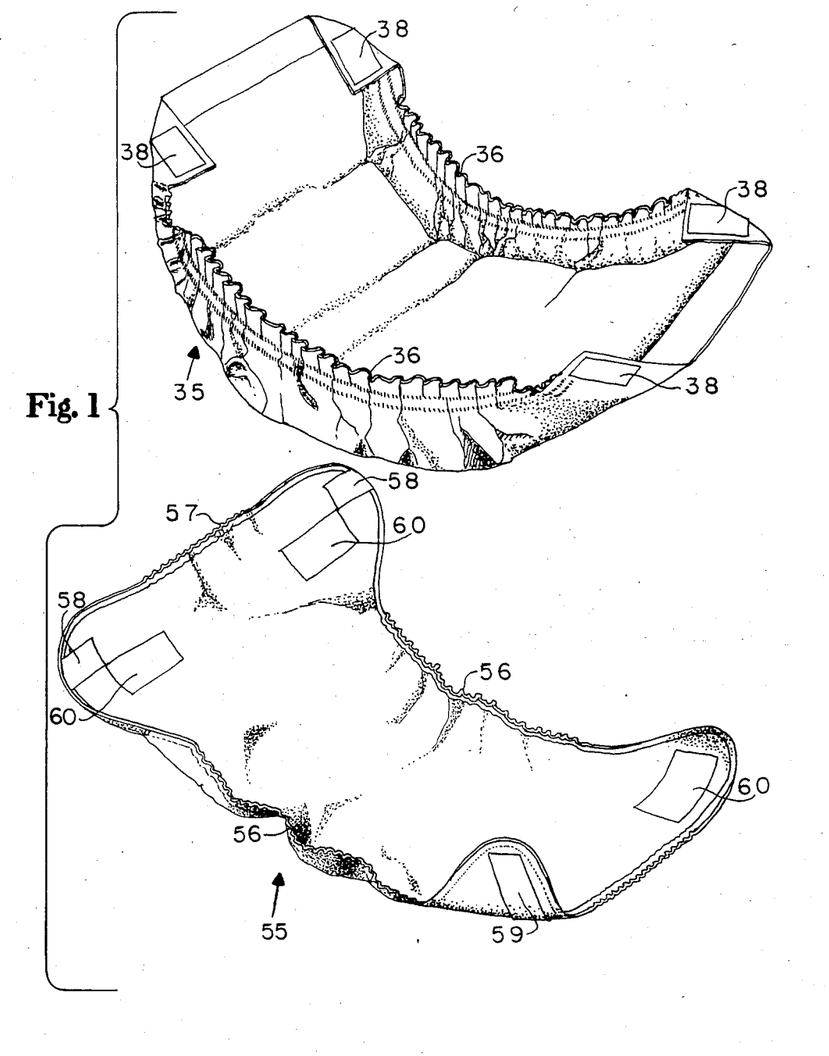
FIG. 1 is an exploded perspective view of an exemplary, 2-element waste-containment garment embodiment of the present invention which comprises a disposable elasticized leg-cuff insert, and side-closing overpants.

An exemplary embodiment of the present invention is shown in FIG. 1 to be a waste-containment garment 31 which comprises an insert 35, an over-garment such as overpants 55, and means for securing such an insert inside a suitable over-garment.

Briefly, insert 35, FIG. 1, may be secured inside suitable over-garments by integral means such as adhesive areas, or by fastener means integral with the over-garment which may cooperate with elements of the insert: for example, grommets disposed on the corners of the insert which may be perforated to cooperate with over-garment mounted snap fasteners or the like, and which grommets may have adhesive coated outer surfaces with peelable covers thereon whereby such an insert would have a duplex capability. That is, be compatible with over-garments not having fasteners by virtue of the adhesive coatings on the grommets; and be compatible with over-garments having fasteners by virtue of the grommets per se. Such combinations are referred to herein as composite garments. Only the insert of such a composite garment needs to be changed upon light soiling as by low volume liquid or solid voiding by the wearer inasmuch as the elastic leg cuffs 36 of the insert 35 generally protect the other garment members from soiling. However, both the insert 35 and the overpants may have to be changed following heavier voiding. For such events, the outer-garment preferably comprises elasticized leg cuffs as well as a general liquid impervious construction to protect the wearer's other clothing from being soiled.

FIG. 1 also shows, in perspective, overpants 55 having elasticized leg cuffs 56; elasticized back-waistband 57; hook and loop type side-closure fastener means such as Velcro (registered trademark of Velcro USA Inc.) which comprise swatches 58 of hook-type fastener material which have been sewn to the inside of the back corners of the overpants and swatches 59 of loop-type fastener material which have been sewn to each outside front corner of the overpants but only one of which swatch 59 is visible in FIG. 1; and landing pads 60 disposed on each inside corner of the overpants and which are made from material which will provide releasable applications thereto of the adhesive areas 39 on insert 35. Such landing pads are spaced equal to the uncontracted spacing of the adhesive areas on insert 35 whereby, upon application of the composite garment to a wearer, the leg cuffs 36 of insert 35 are automatically properly tensioned in sealing relation with skin areas of the wearer. Such overpants preferably have a liquid impervious construction which may comprise a liquid impervious layer of material disposed outside of a soft fabric topsheet (i.e., innermost ply), and which may have a soft fabric backsheet (i.e., outmost ply which may be decoratively adorned with lace and the like, not shown. An exemplary quality overpants comprising Velcro side-closure means, elasticized leg cuffs, and an elasticized back-waistband is marketed in a variety of sizes by Nishiki K.K. under the Brand name of Semi Cot Proof in Japan. This has a generally liquid impervious construction although its leg cuffs are believed to be a breathable, porous construction.

Figure 2:
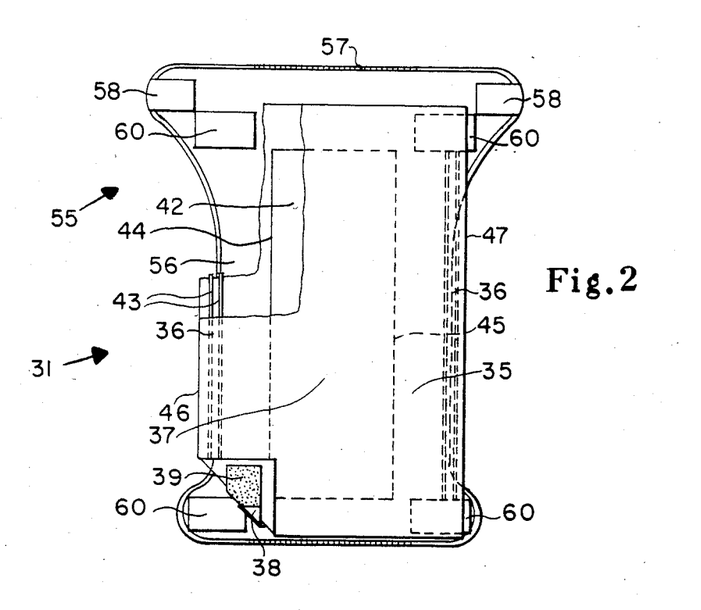
FIG. 2 is a plan view of the waste-containment garment shown in FIG. 1, and with some areas torn away to reveal underlying structure.

FIG. 2 is a composite plan view of an exemplary composite waste-containment garment 31 comprising the insert 35, and overpants 55, FIG. 1, in assembled relation with the topsheet 41 of insert 41 facing upwardly, and with various portions torn away to reveal the underlying structure as described above. As shown in FIG. 2, insert 35 of exemplary composite waste-containment garment 31 is wider when stretched to remove its elastic induced contraction than the underlying structure of overpants 55. However, as explained more fully in describing FIG. 7 below, the leg cuffs 36 of the insert are positioned to be inboard of the leg cuffs 56 of the overpants when the garment 31 is secured on a wearer.

Figure 3:
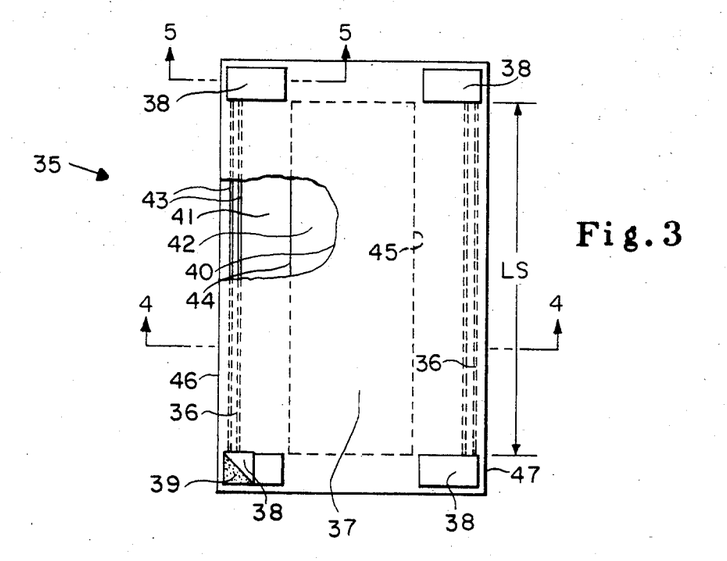
FIG. 3 is a plan view of the insert shown in FIG. 1 which view is taken looking at the outwardly facing surface of the backsheet of the insert with the insert in a non-contracted state: i.e., flat out rather than being contracted by the strands of elastic disposed in its leg cuff areas.

Referring now to FIG. 3, an exemplary waste-containment insert 35 is shown to comprise elasticized leg cuffs 36, and a backsheet 37 having a captive peelable cover member 38 covering an adhesive area 39 disposed on each of its four corners, one cover 38 being partially peeled back in FIG. 3 to reveal one of the four adhesive areas 39. Additionally, as shown in FIG. 3, a portion of backsheet 37 is torn away forming torn edge 40 which reveals the structure of insert 40 disposed behind backsheet 37 in FIG. 3. Such structure includes topsheet 41, absorbent core 42, and elastic strands 43, core side edges 44 and 45, and insert side edges 46 and 47.

An exemplary insert 35 was constructed in which the backsheet 37 is a matte-finish polyethylene film having a nominal thickness of about one mil (about 0.0254 mm), and overall length and width of about fifteen inches by about eight inches, respectively (about 38.1 by 20.3 cm, respectively) the topsheet 41 is a non-woven polypropylene also having a nominal thickness of about one mil, and length and width about equal to the corresponding dimensions of the backsheet; an air laid fibrous core having a nominal weight of about 30.7 grams, a nominal caliper of about 7.1 mm, and length and width of about thirteen by four inches, respectively (about 33 by 10.2 cm, respectively); strands 43 of elastic having nominal unstretched thickness and width of about 0.2 and 2.4 mm, respectively, and which had been stretched about one-hundred-twenty-five percent (125%) prior to being adhesively secured to the backsheet, and prior to adhesively securing the topsheet to the backsheet whereby the longitudinal side edges of the insert (i.e., the elasticized leg cuffs 36) have nominal extensions (i.e., their available stretch as a percent of their elastically contracted length) of about one-hundred-twenty-five percent. Additionally, the core is enveloped with a low basis weight tissue paper not shown to provide structural integrity.

As further shown in FIG. 3, the elastic strands 43 extend longitudinally between the adhesive areas which are covered with peelable covers 38, and the strands 43 are disposed adjacent the superimposed longitudinal side edges 46 and 47 of the insert. In the exemplary insert, the inboard edge of the elastic strand 43 disposed closest to the absorbent core 42 is spaced therefrom about one-and-seven eighths inches (about 4.76 cm) whereby the elasticized leg cuffs—being relatively wide—can be contracted and stretched without having to induce crumpling or longitudinal compression of the core. Thus, stretching induced tension is available for sealingly engaging the leg cuffs 36 with skin areas of a wearer rather than being vitiated by trying to longitudinally compress the core. FIG. 3 also shows that portions of the covered adhesive areas are disposed in longitudinal alignment with the elastic strands 43, and that the adhesive areas having covers 38 are longitudinally spaced a distance LS apart. In the exemplary insert LS is about thirteen inches (about 33 cm).

Figure 4:
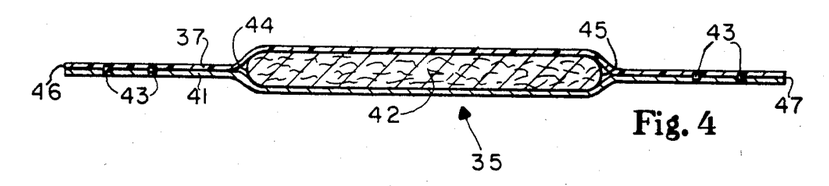
FIG. 4 is a fragmentary sectional view taken along line 4—4 of FIG. 3.

FIG. 4 is a transverse sectional view taken along line 4—4 through the waste-containment insert 35, FIG. 3. As shown in FIG. 4, the backsheet 37 and topsheet 41 of insert 35 are joined together along the longitudinal side edges 44 and 45 of absorbent core 42 and coextensively extend outwardly therefrom. Elastic strands 43 are secured intermediate topsheet 41 and backsheet 37 adjacent the longitudinal side edges 46 and 47 of insert 35. Thus, the laminated regions of the backsheet and topsheet disposed outboard of edges 44 and 45 are generally referred to as elasticized cuffs due to the pliability of the topsheet and the backsheet in combination with the elasticity of the elastic strands 43. However, the most effective portion of these cuffs with respect to liquid sealing is the portion disposed immediately adjacent the elastic strands. Thus, lines of tension induced sealing are principally disposed—when the insert is applied to a wearer as described hereinbefore—intermediate the outer surface of topsheet 41 and the skin of the wearer in the zones disposed between the pairs of elastic strands: one line or band of sealing for each pair of elastic strands.

Figure 5:
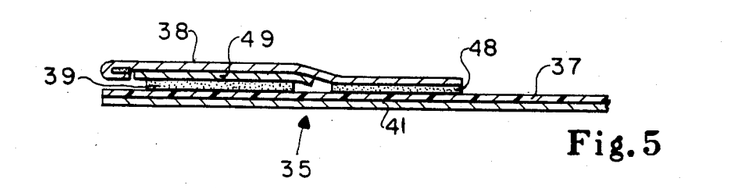
FIG. 5 is a fragmentary sectional view taken along line 5—5 of FIG. 3.

FIG. 5, taken along section line 5—5, FIG. 3, shows an adhesive area 39 on a corner of the backsheet 37 of a fragmentary portion of an insert 35, FIG. 3, and a captive peelable cover 38 disposed in its factory applied position. In this position, one end of the cover 38 is permanently (i.e., non-releasably) adhered to the backsheet 37 with adhesive 48; and the other end of the cover 38 is coated with a release coating 49 which renders the cover peelable from adhesive 39, but captive with respect to the insert even after being peeled from adhesive 39.

Figure 6:
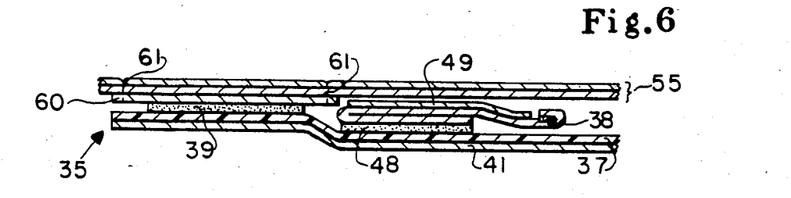
FIG. 6 is a fragmentary sectional view of the adhesive fastener area shown in FIG. 5 after the cover for the adhesive has been peeled back and the adhesive area secured to the surface of one of the landing-pads which are incorporated in an over-garment such as shown in FIG. 1.

FIG. 6 is a fragmentary sectional view which, essentially, shows the structure of FIG. 5 after the cover 38 has been peeled back to uncover adhesive 39, and after adhesive 39 has been secured to a landing pad 60 sewn to a portion of the inwardly facing surface of overpants 55 with lines of stitching 61. Thus, covers 38 of insert 35 are captive: permanently joined to insert 35 to obviate severable members which might present a trash disposal problem or, perhaps, precipitate a safety problem.

Figure 7:
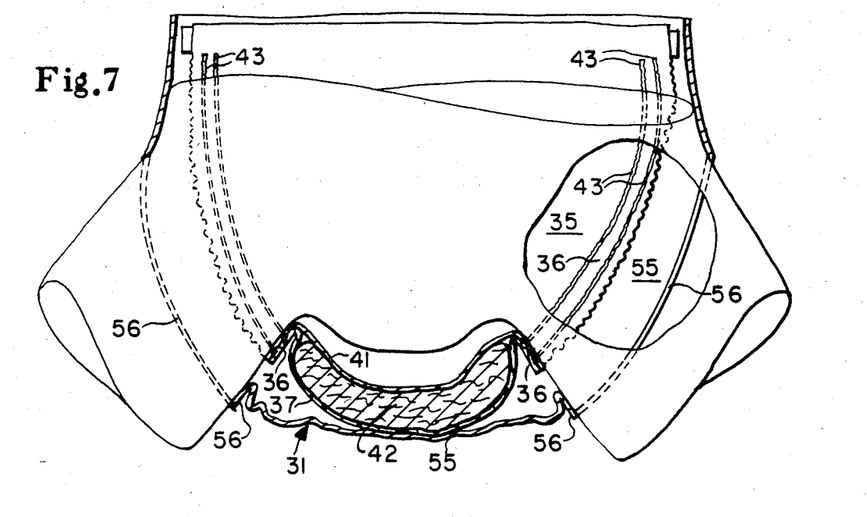
FIG. 7 is a fragmentary, side-to-side vertical sectional view of the waste-containment garment of FIGS. 1 and 2 secured about a fragmentary portion of a wearer: i.e., the lower torso and upper thighs of an infant.

FIG. 7 is, as stated hereinbefore, a fragmentary, side-to-side vertical sectional view of the composite waste-containment garment 31 of FIG. 1 secured about a fragmentary portion of a wearer comprising the lower torso and upper thigh portions of the wearer. As described above, when garment 31 is applied to a wearer and secured in place with the side-closure fasteners of overpants 55, the leg cuffs 56 of the overpants are dressed (i.e., manually positioned) to be outboard of the leg cuffs 36 of the insert. Thus, garment 31 comprises two sets of independently elasticized leg cuffs which are jointly tension energized upon securing the garment about a wearer, and which leg cuffs are in serially disposed relation. That is, for liquid to leak from the garment, it must serially (i.e., sequentially) pass a line-of-sealing effected by a leg cuff 36 and another line-of-sealing effected by a leg cuff 56.

Figure 8:
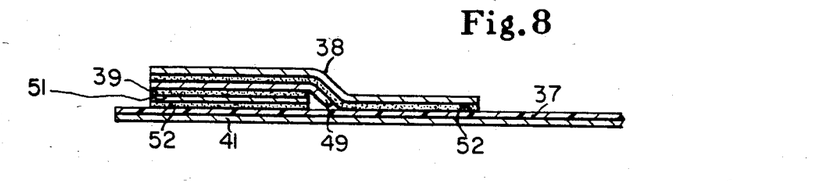
FIG. 8 is a fragmentary sectional view of an insert such as shown in FIG. 3 having an alternate adhesive fastener which view is similar to FIG. 5.
Figure 9:
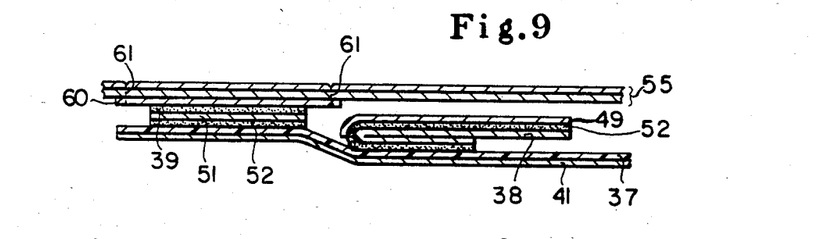
FIG. 9 is a fragmentary sectional view of the alternate adhesive fastener embodiment of FIG. 8 after it has been secured to a landing-pad in an over-garment which view is similar to FIG. 6.

FIGS. 8 and 9 are similar to FIGS. 5 and 6, respectively, except the adhesive area 39 of FIGS. 5 and 6 has been replaced by a piece of double sided adhesive tape (i.e., a piece of tape 51 having adhesive 52 on one side and adhesive 39 on its other side), and cover 38 comprises a strip of tape having an adhesive coating 53 on its entire facing surface. Thus, functionally, the structures are believed to be functionally equivalent albeit adhesive 39 of the FIG. 5 structure is applied directly to spaced areas of backsheet 37 whereas the structure of FIG. 8 is achieved by applying pieces of the double sided adhesive tape to spaced areas of the backsheet, and by applying pieces of cover tape 38 as shown in the drawings.

Figure 10:
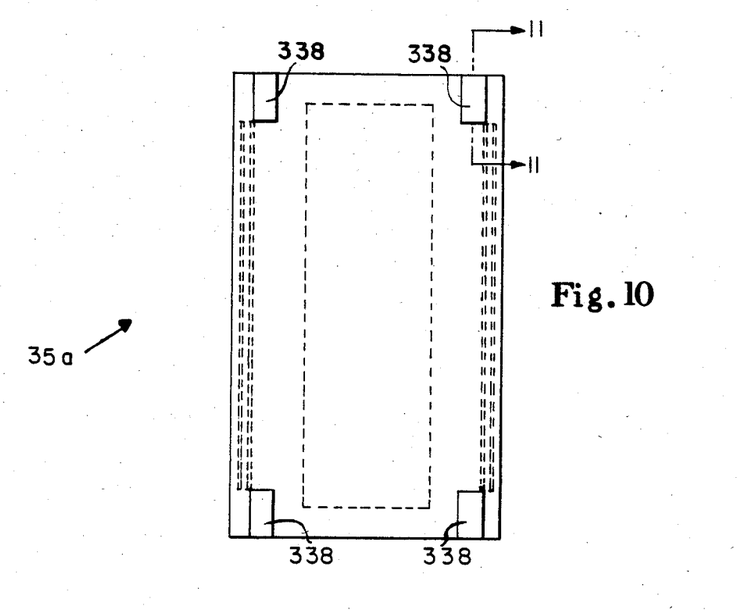
Figure 13:
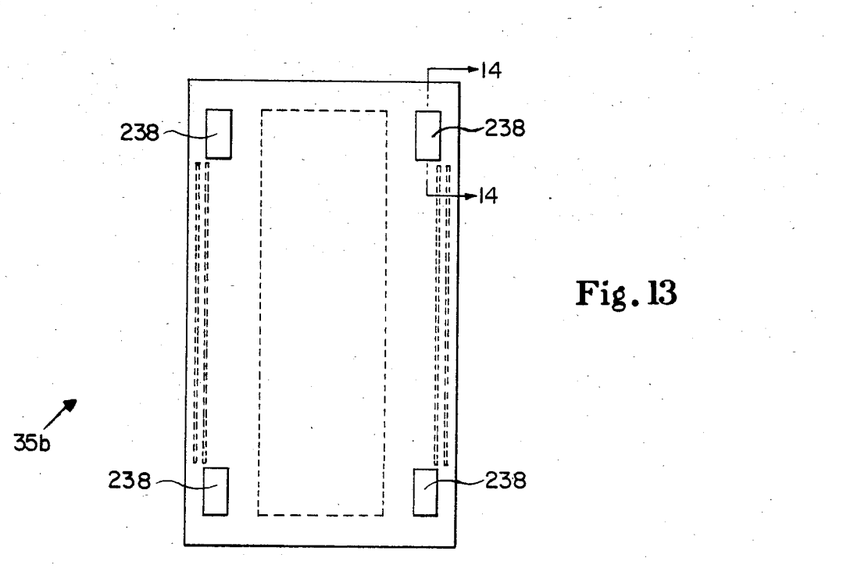

FIGS. 10 and 13 are plan views of waste-containment insert embodiments 35a and 35b, respectively, of the present invention which are like insert 35, FIG. 3, but for the construction of their tape fasteners. In FIGS. 10 and 13, the visible portions of the tape fasteners are designated 338 and 238, respectively.

Figure 11:
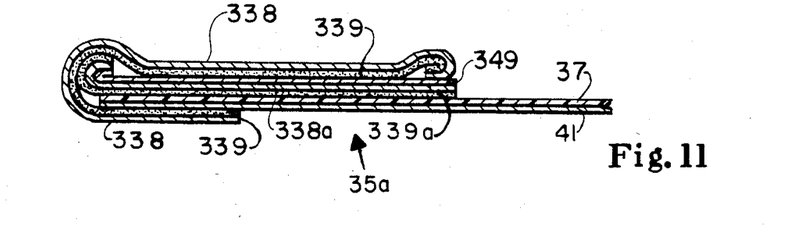
FIGS. 11, 12, 14 and 15 are sectional views which show inserts such as shown in FIG. 3 having additional alternate embodiment adhesive fasteners.
Figure 12:
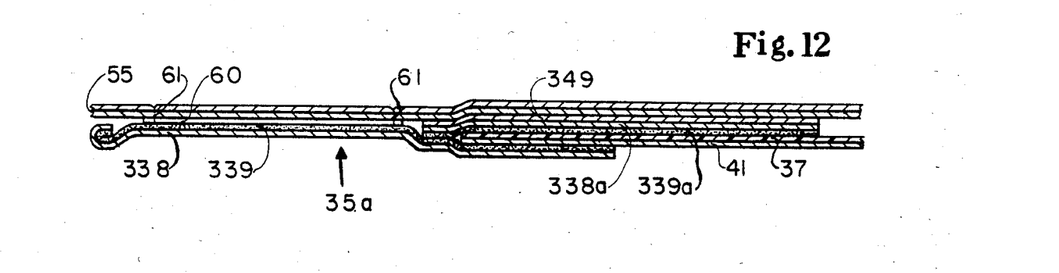

FIG. 11 is a sectional view taken along line 11—11 of FIG. 10. This shows an adhesive tape fastener of insert 35a, FIG. 10, in its factory applied state. It comprises cover tape 338 having an adhesive coating 339, a secondary tape 338a having adhesive coating 339a on one surface and a release coating 349 on its other surface. When used, the folded-under grasping portion of tape 338 is grasped and tape 338 along with adhesive coating 339 is peeled from release coating 349. The adhesive coated peeled portion of tape 338 is then applied to the inwardly facing surface of a landing pad 60 of overpants 55 as shown in FIG. 12. Such a tape fastener is generically referred to as a Y-tape and is substantially identical to Y-tapes used on disposable diapers except the free adhesive-coated end of the present tape fastener faces outwardly whereas those of disposable diapers face inwardly. Additionally, it is obvious from the figures that the spacing of the adhesive areas on insert 35a would require greater spacing of the landing pads 60 on overpants 55 than for insert 35 described above.

FIG. 13 shows a tape fastener which is spaced from the end of insert 35b rather than being Y-formed over the end edge of the insert 35a, FIG. 10.

Figure 14:
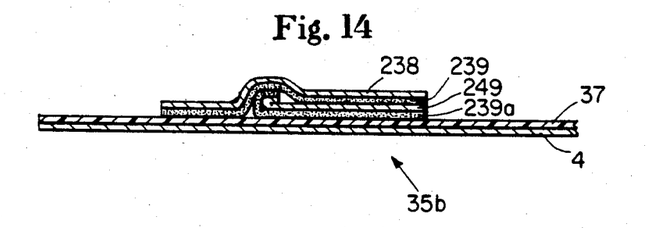
Figure 15:
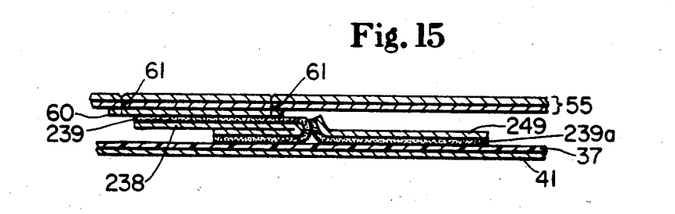

The tape fastener shown in FIG. 14 comprises cover tape 238 having an adhesive coating on its entire inwardly facing surface, and release tape 249 adhesively secured to the backsheet 37 of insert 35b with adhesive 239a. One end of cover tape 238 is permanently bonded to backsheet 37 and the other end is releasably adhesively secured to the outwardly facing surface of release tape 249. The latter end is peeled from release tape 249 and applied to a landing pad 60 of overpants 55 as shown in FIG. 15 when an insert is secured in such overpants. The tape fasteners of this embodiment can be spaced to be compatible with overpants 55 having landing pads properly spaced for compatibility with inserts 35.

Figure 16:
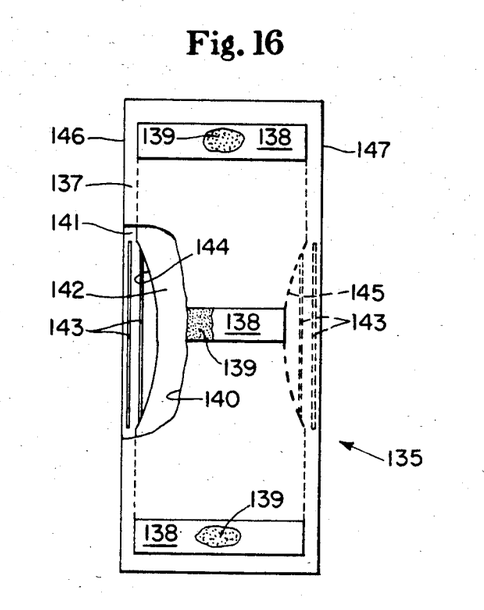
FIG. 16 is a plan view of an alternate insert embodiment of the present invention looking at the outwardly facing surface of the backsheet thereof, and having portions of the backsheet torn away to reveal underlying structure.

FIG. 16 is a plan view of an alternate embodiment insert 135 which may be used to practice the present invention. The features of insert 135 which have counterpart features in insert 35 have the same designators increased by 100: e.g., insert 35 versus insert 135. Insert 135 is preferably constructed of the same materials (i.e., topsheet material, backsheet material, elastic strands, and absorbent core) as insert 35, FIG. 3. However, insert 135 exemplifies very low cost executions wherein the overall plan-view size is little more than the plan-view size of core 142; and the core is very thin and light. For example, an exemplary core having width and length dimensions of about five-and-one-half inches by about fourteen inches (about 14 by 36 cm), respectively, has been provided having a nominal thickness of about 1.4 mm and an airfelt weight of about 14.4 grams. This embodiment has concave edges in the crotch region with a minimum width of about four inches (about 10 cm). As indicated in FIG. 16, insert 135 has three adhesive areas 139 having peelable covers 138; and its leg flaps 136 are only elasticized adjacent the crotch region although it is not intended to thereby limit the present invention. Indeed, it is believed that adhesive areas disposed in the four corners would be sufficient for energizing the elasticized leg cuffs as with insert 35. As with insert 35, the width of core 142 is preferably in the range of from about 15 percent to about 35 percent of the waistband girth of a prospective wearer with the waistband width being somewhat greater than one-quarter the waistband girth of a wearer of average size and the crotch width being somewhat less: e.g., five-and-one-half inches and four inches, respectively, as stated above.

Figure 17:
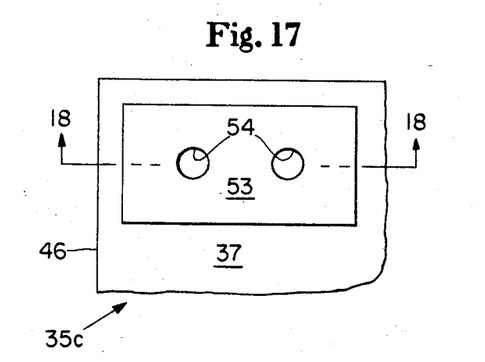
FIG. 17 is a plan view of a fragmentary corner portion of an alternate embodiment insert having a two-hole reinforcing grommet secured to its outwardly facing surface.

FIG. 17 is a plan view of a fragmentary portion of an alternate embodiment 35c of the insert 35, FIG. 2. Inserts 35 and 35c are alike but for the covers 38 of insert 35 being replaced with a grommet 53 having 2 holes 54 in it. Such a grommet is sized and configured to enable snap fasteners of snap-fastener equipped overpants to be secured through one of the holes whereby the insert is secured within such overpants. The grommet is secured to the backsheet 37 as with adhesive or heat sealing or the like, adhesive 39a being shown in FIG. 18. Such grommets may be made from Mylar (registered TM of DuPont) or other tape having adequate strength to sufficiently reinforce the corners of the insert to survive the stresses imposed by snap fasteners.

Figure 18:
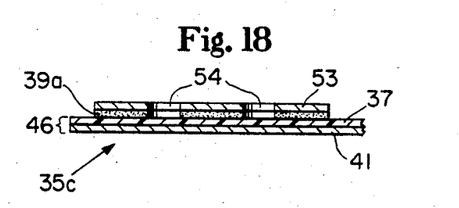
FIG. 18 is a fragmentary sectional view taken along line 18—18 of FIG. 17.
Figure 19:
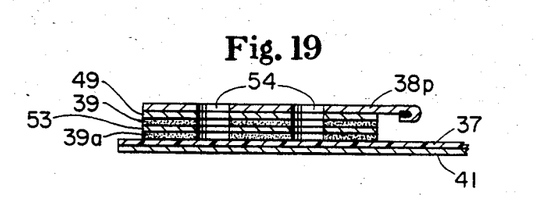
FIG. 19 is a fragmentary sectional view similar to FIG. 18 but wherein the outwardly facing surface of the reinforcing grommet is adhesive coated, and which adhesive coating is covered with a peelable cover member.

FIG. 19 is a sectional view of a variant of the grommet embodiment shown in FIG. 18. However, in the FIG. 19 variant, the grommet 53 is coated with adhesive 39 which is covered with a peelable cover 38p. This variant would enable the insert to be adhesively secured in over-garments not having integral fastener means, or in overpants having snap fasteners as described above.

Figure 20:
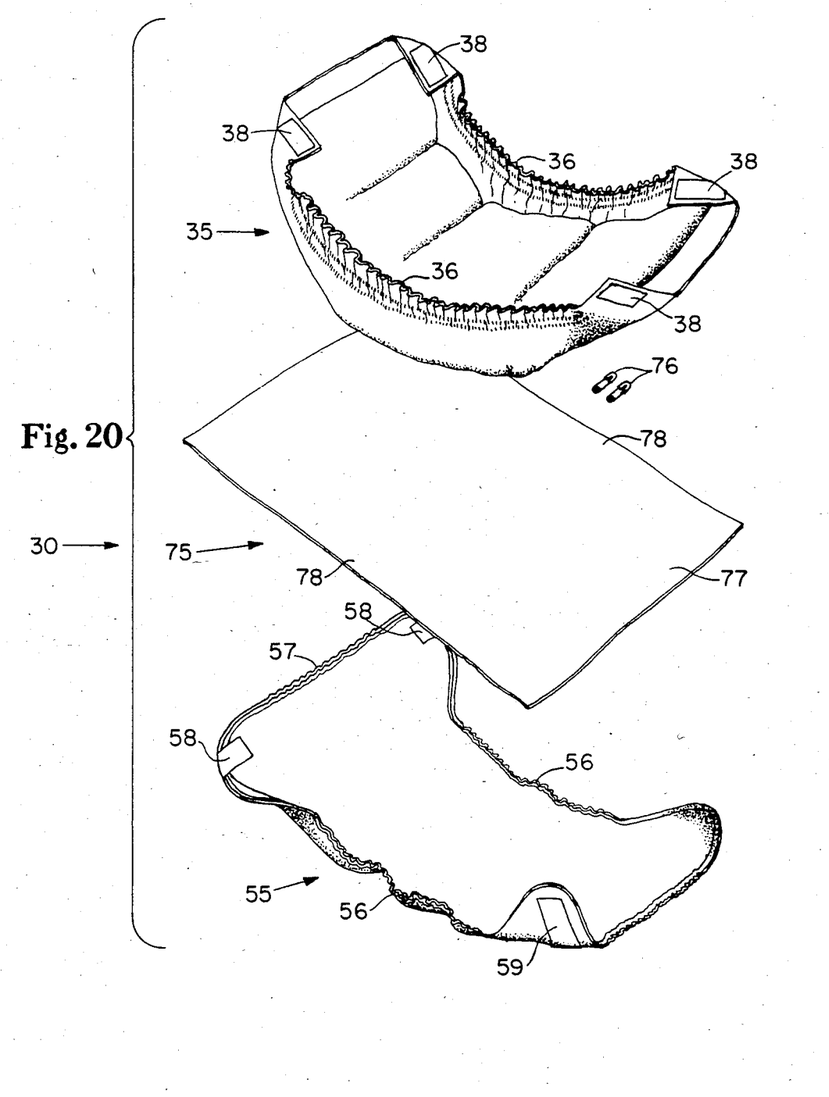
FIG. 20 is a perspective exploded view of a 3-element composite waste-containment garment.

FIG. 20 is a 3-element composite waste-containment garment 30 which comprises a waste-containment insert such as insert 35, FIG. 3; an outer-garment such as overpants 55, FIG. 1; an over-garment such as a conventional cloth diaper 75; and means such as safety pins 76 for securing the diaper about a user after an insert has been secured to the inwardly facing surface of the diaper. However, the overpants 55 as shown in FIG. 20 are devoid of the landing pads 60 of FIG. 1 inasmuch as the insert is not directly secured to the overpants in the FIG. 20 configuration.

Briefly, to use the exemplary 3-element garment 30, FIG. 20, an insert 35 is secured to the inwardly facing surface 77 of the diaper 75 by means integral with the insert after the insert has been sufficiently stretched to substantially reduce its elastic induced contraction. Then the diaper (having an insert secured therein) is applied to and secured about a wearer so that the elastic leg cuffs 36 of the insert 35 are sealingly engaged or juxtaposed skin areas of the wearer by stretching induced tension in the elasticized leg cuffs. The over-garment 55 is then applied to entirely cover the combination of insert 35 and diaper 75, and side closures of the overpants 55 are secured. Finally, the elements of the composite garment are dressed (i.e., manually positioned) so that the longitudinally extending side edge regions 78 of diaper 75 are disposed intermediate the leg cuffs 36 and the leg cuffs 56, and so that all (i.e., 36, 56 and 78) are in contacting relation with the wearer's skin. Only the insert of such a composite garment needs to be changed upon light soiling as by low volume liquid or solid voiding by the wearer inasmuch as the elastic leg cuffs 36 of the insert 35 generally protect the other members 55 and 75 of the garment 30 from soiling.

Figure 21:
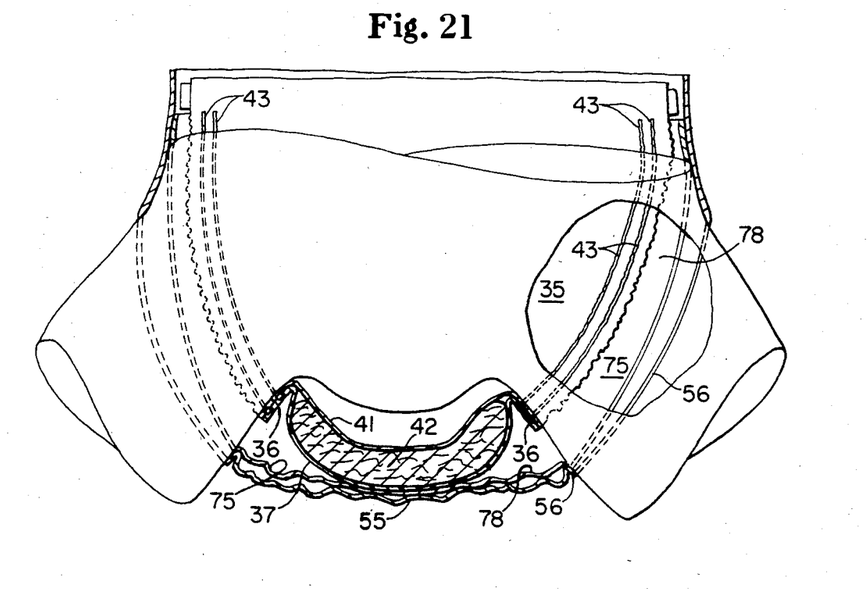
FIG. 21 is a fragmentary sectional view similar to FIG. 7 but wherein the 3-element composite waste-containment garment of FIG. 20 has been applied to a fragmentary portion of a wearer.

FIG. 21 is a fragmentary, side-to-side vertical sectional view of the composite waste-containment garment 30, FIG. 20, which is secured about a fragmentary portion of a wearer. The garment was applied by first securing an insert 35 to a diaper 75 as described above in conjunction with describing FIG. 20; then that subassembly was pinned on the wearer as also described above; and then the overpants 55 were secured in place over the diaper upon fastening its side closure fasteners. The leg cuffs 36 and 56, of the insert 35 and overpants 55, respectively, and the longitudinal side edge regions 78 of the diaper 75 were then manually positioned so that all were in skin contracting relation with the wearer, and so that each side edge region 78 was disposed intermediate a leg cuff 36 of the insert and a leg cuff 56 of the overpants. Thus positioned, the diaper will wick liquid that passes cuffs 36 and thereby substantially obviate an accumulation of liquid which might otherwise breach cuffs 56 and soil the clothing of the wearer.

The composite garments 30 and 31 as described above comprise side-closure overpants. However, it is not intended to thereby limit the present invention.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A waste-containment garment comprising an over-garment, an insert having elasticized leg cuffs and a liquid impervious backsheet, and means for securing said insert inside said over-garment so that said leg cuffs of said insert are sealingly tensioned in juxtaposition with skin areas of the wearer when said over-garment having a said insert secured therewithin is applied to a wearer, said means for securing being incorporated in said insert, and said means for securing comprising adhesive means disposed on the outwardly facing corners of said insert and wherein landing-pad members are secured in spaced relation to the inwardly facing surface of said over-garment, said spaced relation being substantially equal to the spaced relation of said adhesive means on said insert when said insert is in a non-contracted state.

* * * * *